United States Patent
Zhou et al.

(10) Patent No.: US 11,141,732 B2
(45) Date of Patent: Oct. 12, 2021

(54) KIT FOR QUICKLY DETECTING LEAD CONTENT IN SAMPLE

(71) Applicant: Beijing Diagreat Biotechnologies Co., Ltd., Beijing (CN)

(72) Inventors: Jianping Zhou, Beijing (CN); Yanxin Wang, Beijing (CN); Yujun Zhou, Beijing (CN)

(73) Assignee: Beijing Diagreat Biotechnologies Co., Ltd., Beijing (CN)

( * ) Notice: Subject to any disclaimer, the term of this patent is extended or adjusted under 35 U.S.C. 154(b) by 0 days.

(21) Appl. No.: 16/726,006

(22) Filed: Dec. 23, 2019

(65) Prior Publication Data
US 2021/0094030 A1    Apr. 1, 2021

(30) Foreign Application Priority Data
Sep. 26, 2019  (CN) .......................... 201910916128.5

(51) Int. Cl.
G01N 33/543    (2006.01)
B01L 3/00      (2006.01)
G01N 33/548    (2006.01)
G01N 33/84     (2006.01)

(52) U.S. Cl.
CPC ............ B01L 3/508 (2013.01); G01N 33/548 (2013.01); G01N 33/54306 (2013.01); G01N 33/84 (2013.01); B01L 2300/025 (2013.01); B01L 2300/069 (2013.01);
(Continued)

(58) Field of Classification Search
None
See application file for complete search history.

(56) References Cited

U.S. PATENT DOCUMENTS

2002/0106708 A1* 8/2002 Thomas ................. G01N 33/86
                                                    435/7.93
2009/0203151 A1* 8/2009 Matsuno .......... G01N 33/54386
                                                    436/518
(Continued)

FOREIGN PATENT DOCUMENTS

CN        101592597 A1    12/2009

OTHER PUBLICATIONS

David A. Lawrence, "In Vivo and In Vitro Effects of Lead on Humoral and Cell-Mediated Immunity," Infection and Immunity, vol. 31, No. 1, Jan. 1981, pp. 136-143.

*Primary Examiner* — Rebecca M Giere
(74) *Attorney, Agent, or Firm* — Klarquist Sparkman, LLP

(57) ABSTRACT

A detection kit for quickly detecting a lead content lead a sample is provided, and belongs to the technical field of medical in vitro immunoassay. The kit includes a detection card and a quality control; the detection card includes a bottom plate, and a sample pad, a glass fiber membrane, a nitrocellulose membrane and an absorbent paper which are arranged on the surface of the bottom plate sequentially from a loading end. The provided kit has advantages of having simple preprocessing, having no need of digestion, and being economic, fast and convenient, and the like, can realize storage at room temperature, a rapid speed, a high throughout, a low instrument cost, simple and convenient operations, single-person packaging, and detection at any time, which greatly improves the simplicity and convenience of clinical use.

11 Claims, 3 Drawing Sheets

(52) U.S. Cl.
CPC ............... *B01L 2300/0627* (2013.01); *B01L 2300/0851* (2013.01); *B01L 2300/12* (2013.01); *B01L 2300/16* (2013.01)

(56) References Cited

U.S. PATENT DOCUMENTS

| | | | |
|---|---|---|---|
| 2013/0102003 A1* | 4/2013 | Gibbs | G01N 33/558 435/6.11 |
| 2015/0160219 A1* | 6/2015 | Davis | G01N 33/543 506/9 |

* cited by examiner

KIT FOR QUICKLY DETECTING LEAD CONTENT IN SAMPLE

CROSS REFERENCE TO RELATED APPLICATION

This application claims the benefit of and priority to Chinese Patent Application No. 201910916128.5, entitled "KIT FOR QUICKLY DETECTING LEAD CONTENT IN SAMPLE," which was filed on Sep. 26, 2019. The entirety of Chinese Patent Application No. CN 201910916128.5 is incorporated herein by reference as if set forth fully herein.

TECHNICAL FIELD

The disclosed subject matter relates to the technical field of medical in vitro immunoassay, and particularly relates to a detection kit for quickly detecting a lead content in a sample.

BACKGROUND

Lead (Pb) is a heavy metal ion with a cumulative effect and polyaffinity, which can cause damage to hematopoietic, digestive, nervous, immune and the like systems of human body. The heavy metal lead is a harmful substance with persistent toxicity, which is difficult to be degraded by biological, chemical and the like methods in a natural environment. When the heavy metal lead enters the human body through a diet, it will be accumulated in the human body and then cause poisoning. Chronic lead poisoning of the human body is exhibited as anorexia, anemia, diarrhea, emaciation, joint pain, etc.; and lead injury is internationally recognized as the first killer that endangers the development of children's nervous systems. When the blood lead content in the body of a child exceeds 100 µg/L, accordingly the intelligence index will drop by 10-20 points. Especially after an infant absorbs the lead, more than 30% of the lead will be remained in the body, which affects the growth and intellectual development of the infant, impairs the cognitive function, neurological behavior, learning and memorizing and the like brain functions, and in serious cases causes dementia. The heavy metal lead has been listed as a mandatory food pollutant test item in the Global Monitoring for Environment and Security (GMES). China has included lead pollution into one of the contents which should be prevented and controlled in "Twelve-Five planning." Therefore, the establishment of an accurate and effective lead determination method has important practical significance and application values.

The traditional lead detection methods can be divided into three categories, a physical detection method, a chemical detection method and a biological detection method, respectively. The detection technology includes spectrum detection, electrophoresis instruments, detection by liquid chromatography, dithizone contrast method, etc. These detection methods have certain advantages in detection accuracy and have extremely-high accuracy, but the detection process is complex and has a high cost, which is difficult to develop in practical application fields. In the aspect of blood lead detection, detection methods with the tungsten boat elemental analyzer for lead and cadmium and the graphite furnace atomic absorption spectrophotometer are more commonly used. The graphite furnace atomic absorption spectrophotometer is equipped with an automatic sampler, has accurate sample determination results and has good precision, but it has strict requirements of experimental conditions and demands for a large current and high voltage. The graphite furnace has an input power of 4000 VA and an input voltage of 380 V. The graphite tube is consumable and easy to damage, and thus is suitable for use in a laboratory with good conditions.

Currently, in 30 provincial and municipal medical institutions of China, in clinical examination a tungsten boat elemental analyzer for lead and cadmium is widely used for measuring blood lead. This instrument is an atomic absorption spectrometer specialized for detecting blood lead by using the tungsten boat as an atomizer (Beijing Bohui Innovation Biotechnology Co., Ltd.). The measured sample is atomized in the tungsten boat by electric heating, so as to generate a large number of ground-state free atoms, thereby absorbing the characteristic spectral line of a measured element emitted by a hollow cathode lamp, and completing the measurement process. A lens glass cover for an atomization cell will be polluted by the adsorption of smoke. At this time, due to the vibration of a solenoid valve, a contaminant may fall into the tungsten boat and thus cause an error. Therefore, during a large number of continuous detections, the detection should be stopped at any time for cleaning as desired, especially during a large number of detections for detecting samples with a high content of lead. As the number of uses of the tungsten boat increases, the tungsten boat is gradually thinning. It is possible that an error in a detection result is caused due to sample splashing resulting from too high and too fast temperature rising during the work. Therefore, when the tungsten boat has been used more than 10 times, the temperature of the tungsten boat should be re-adjusted or a new tungsten boat should be replaced, and meanwhile a standard curve is redone; with the use of an element lamp, its luminous intensity will gradually decrease, and its stability may also decrease. Therefore, it is not appropriate to use the element lamp continuously for too many times after completion of the standard curve. A national reference material should be added every 10 uses to monitor the sensitivity of the element lamp. If the sensitivity is reduced or the energy value is unstable, the standard curve should be redone or the element lamp should be replaced. This detection method has disadvantages of being not capable of detecting a sample with a high throughput, requiring frequent replacement of the element lamp, having a high detection cost, and having cumbersome operations.

SUMMARY

An example practical application of the disclosed subject matter is to provide a detection kit for quickly detecting a lead content in a sample. The disclosed kit has advantages of having simple preprocessing, having no need of digestion, and being economic, fast and convenient, and the like, can realize storage at room temperature, a rapid speed, a high throughout, a low instrument cost, simple and convenient operations, single-person packaging, detection at any time, and high stability, which can greatly improve the simplicity and convenience of clinical use.

According to one aspect of the disclosed technology, the disclosed subject matter provide a kit for rapidly detecting a lead content in a sample. The kit can include a detection card and a quality control; wherein the detection card can include a bottom plate, and a sample pad, a glass fiber membrane, a nitrocellulose membrane and an absorbent paper which can be arranged on the surface of the bottom plate sequentially from a loading end;

the sample pad can be treated by soaking in a sample pad treatment buffer, and the sample pad treatment buffer can include an active protein and a surfactant;

the glass cellulose membrane can be coated with: a conjugate of a lead specific antibody and a fluorescent microsphere, and a conjugate of a chicken IgY antibody and a fluorescent microsphere;

the nitrocellulose membrane can be marked with a detection line and a quality control line, the detection line can be coated with a lead-conjugated hapten, and the quality control line can be coated with a goat anti-chicken IgY antibody.

In some embodiments, the sample pad treatment buffer can use one or more of a triethanolamine buffer, a boric acid-borate buffer, and a glycine buffer as a basal buffer.

In some embodiments, the active protein can include one or more of fetal bovine serum, horse serum albumin and bovine serum albumin.

In some embodiments, the surfactant includes one or more of S9, S13, and Tween80.

In some embodiments, the ratio of the conjugate of the lead-specific antibody and the fluorescent microsphere to the conjugate of the chicken IgY antibody and the fluorescent microsphere can be (4-7):1.

In some embodiments, the fluorescent microsphere can have a particle size of 80-220 nm.

In some embodiments, the lead-specific antibody in the conjugate of the lead-specific antibody and the fluorescent microsphere can be a lead-specific murine monoclonal antibody.

In some embodiments, a method for preparing the glass cellulose membrane can include: soaking the glass cellulose membrane in a resuspension buffer for 1-2 h, and baking it for 1-2 h to obtain a preprocessed glass cellulose membrane; respectively dissolving the conjugate of the lead specific antibody and the fluorescent microsphere and the conjugate of the chicken IgY antibody and the fluorescent microsphere in the resuspension buffer, spraying the solution onto the preprocessed glass cellulose membrane, and baking; wherein the resuspension buffer can use one or more of a phosphate buffer, a boric acid buffer, and a glycine buffer as a basal buffer of 50-200 mM having a pH value of 5.5-6.8, and further includes 0.5-3 g/L of sucrose and a S9 with a percentage mass content of 0.1%.

In some embodiments, the quality control can be a lead-containing buffer, and the buffer can include the following components: a 0.5 mM nitric acid buffer, Tween 20 with a mass-to-volume ratio of 0.1%, bovine serum albumin with a percentage mass content of 0.5%, Proclin300 with a percentage mass content of 0.1%, and water as the solvent, with the pH value being 4.8-5.0.

In some embodiments, the quality control can be stored after lyophilization, and a lyophilization buffer for the lyophilization can use a 0.5 mM nitric acid buffer having a pH value of 4.5-4.8 as a basal buffer, and also can include 5-10 g/L of trehalose, 5-20 g/L of mannitol and Proclin300 with a percentage mass content of 0.1%.

The disclosed subject matter provides a detection kit for quickly detecting a lead content in a sample. The disclosed subject matter provides a detection kit for achieving the detection of the lead content in blood by an entirely new immunological methodology, and the kit has advantages of a low detection instrument cost, simple and rapid operations, storage and transportation at room temperature, realization of packaging for a single person, and a good stability. Compared with a differential potentiometric stripping method which has a large matrix interference and complicated operations, the disclosed kit has advantages of using immunochromatography to detect the lead content in blood, which has a low detection instrument cost, avoids the complicated preprocessing process, detects rapidly for only 15 min, can achieve high-throughput detection, is packed for a single person, and has good stability and high repeatability. Compared with a graphite furnace atomic absorption spectrometry which has a large matrix interference and a high price, strict requirements of experimental conditions and demands for a large current, and uses a high-voltage graphite tube that is easily damaged and thus is a consumable, the disclosed kit has a low detection instrument cost, simple operations, and reagents capable of being stored at room temperature. Compared with a method for detecting a lead element in whole blood by a tungsten-boat atomic absorption spectrometry (Beijing Bohui Innovation Biotechnology Co., Ltd., granted publication No. CN101592597A), with the principle of the measured sample in the tungsten boat being atomized by electric heating so as to generate a large number of ground-state free atoms, thereby absorbing the characteristic spectral line of a measured element emitted by a hollow cathode lamp, and completing the measurement process, the disclosed kit has advantages of detecting the content of the lead element in a blood sample and a urine sample by the immunochromatography, having a low detection instrument cost, being capable of storing and transporting at room temperature, realizing high-throughput detection, and packing for a single person.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. The foregoing and other aspects and features of the disclosed technology will become more apparent from the following detailed description, which proceeds with reference to the accompanying figures.

The foregoing and other objects, features, and advantages of the invention will become more apparent from the following detailed description, which proceeds with reference to the accompanying figures.

DETAILED DESCRIPTION

Figure 3:
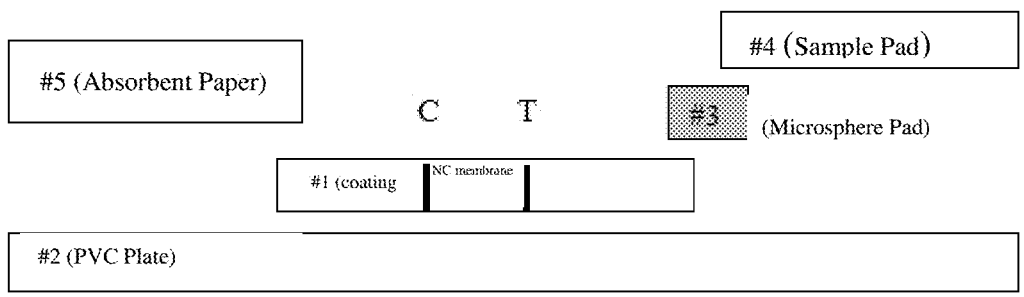
FIG. 3 is a schematic structural view of a detection card in the kit according to one example embodiment.

The disclosed subject matter provides a kit for rapidly detecting a lead content in a sample. The kit can include a detection card and a quality control; wherein the detection card can include a bottom plate, and a sample pad, a glass fiber membrane, a nitrocellulose membrane and an absorbent paper which can be arranged on the surface of the bottom plate sequentially from a loading end. An example embodiment of the detection card is as shown in FIG. 3, wherein 1 represents a nitrocellulose membrane, and specifically a coated NC membrane; 2 represents a bottom plate, and specifically a PVC plate; 3 represents a glass fiber membrane, and specifically a microsphere pad; 4 represents a sample pad; and 5 represents absorbent paper.

As described herein, the sample pad can be treated by soaking in a sample pad treatment buffer, and the sample pad treatment buffer can include an active protein and a surfactant. After treated by soaking in the sample pad treatment buffer, the adsorption of a sample by the sample pad can be reduced. In some embodiments, the sample pad treatment buffer can use one or more of a triethanolamine buffer, a boric acid-borate buffer, and a glycine buffer as a basal buffer. The adoption of these kinds of buffers can provide a buffering capacity, and can correct the difference in pH between individual samples. In some embodiments, the active protein can include one or more of fetal bovine serum, horse serum albumin and bovine serum albumin. The active protein can block an active site on the sample pad, ensuring that target analytes are all flowed out and fully participate in the reaction. In some embodiments, the surfactant can include one or more of S9 (Tetronic 1307), S13 (TRITON X-45 N 10.4 426) and Tween80. The surfactant disclosed herein can improve the detection line and sensitivity of metal ion determination, and can also improve the dispersibility of a sample on a glass fiber membrane. In some embodiments, the time of the soaking treatment can be 1-2 h, and in some embodiments 1 h. In some embodiments, after the soaking treatment, the sample pad can be subjected to a drying treatment, and for example, can be baked at 37° C. The disclosed subject matter can have no special limitation on sources of respective components of the sample pad treatment buffer, and a commercially-available product that is known to those skilled in the art can be adopted.

In some embodiments, the glass cellulose membrane can be coated with: a conjugate of a lead-specific antibody and a fluorescent microsphere, and a conjugate of a chicken IgY antibody and a fluorescent microsphere. In some embodiments, the conjugate of the lead-specific antibody and the fluorescent microsphere can have the function of specifically recognizing the heavy metal lead in the sample, and can form an immune complex with lead, and the immune complex can be chromatographed along the nitrocellulose membrane into a detection zone (T), and bind with the pre-coated lead-conjugated hapten, with its fluorescence intensity being inversely proportional to the lead content in the sample. The conjugate of the chicken IgY antibody and the fluorescent microsphere can be chromatographed into a quality control zone (C) and bind with the pre-coated goat anti-chicken IgY. In some embodiments, the volumetric mixture ratio of the conjugate of the lead-specific antibody and the fluorescent microsphere to the conjugate of the chicken IgY antibody and the fluorescent microsphere can be 4-7:1, and in some embodiments 6:1. In some embodiments, the conjugate of the lead-specific antibody and the fluorescent microsphere and the conjugate of the chicken IgY antibody and the fluorescent microsphere can be adjusted to have a total mass concentration of 0.2% before being sprayed onto the glass cellulose membrane. In some embodiments, the particle size of the fluorescent microsphere can be 80-220 nm, and in some embodiments 120 nm. As disclosed here, the fluorescent microsphere can have the advantages of a large difference between exciting and receiving wavelengths, low interference, high detection sensitivity, and good reproducibility. The fluorescent microsphere disclosed herein can be a conventional commercially-available product. In some embodiments, the lead-specific antibody in the conjugate of the lead-specific antibody and the fluorescent microsphere can be a lead-specific murine monoclonal antibody. Certain aspects of the disclosed subject matter also concern a method for preparing the lead-specific murine monoclonal antibody. The method can include the following steps: 1. a mouse can be injected with an antigen protein (e.g., a lead-conjugated bovine serum albumin), so that the mouse product can be subjected to an immune response; 2. corresponding B lymphocytes can be obtained; 3. mouse myeloma cells can be fused with the B lymphocytes, and then screened with selective media (HAT and HT); 4. after the screening, the cells can be monoclonal cells, which can not only reproduce significantly, but also can produce specific antibodies; 5. the above hybridoma cells can be subjected to monoclonal cultivation and antibody detection, such that cells stably secreting monoclonal antibodies can be obtained after multiple times of screening; and 6. the hybridoma cells can be cultured at a large scale in vitro, or be intraperitoneally injected into a mouse for propagation to produce ascites, such that a large number of lead-specific murine monoclonal antibodies can be obtained after purification.

Certain aspects of the disclosed subject matter also concern a method for preparing the glass cellulose membrane. The method can include: soaking the glass cellulose membrane in a resuspension buffer for 1-2 h, and baking it for 1-2 h to obtain a preprocessed glass cellulose membrane; respectively dissolving the conjugate of the lead specific antibody and the fluorescent microsphere and the conjugate of the chicken IgY antibody and the fluorescent microsphere in the resuspension buffer, spraying the solution onto the preprocessed glass cellulose membrane, and baking; wherein the resuspension buffer can use one or more of a phosphate buffer, a boric acid buffer, and a glycine buffer as a basal buffer of 50-200 mM having a pH value of 5.5-6.8, and further includes 0.5-3 g/L of sucrose and a S9 with a percentage mass content of 0.1%. In some embodiments, the resuspension buffer can have the beneficial effect of removing unconjugated proteins, and the resuspension buffer can provide a suitable pH and an ionic-strength environment to be capable of ensuring that the final antibody-microsphere conjugate has an activity and the antibody is not easily detached. In some embodiments, the baking can be baked at 45-65° C. for 2-6 h.

In some embodiments, the nitrocellulose membrane can be marked with a detection line and a quality control line, the detection line can be coated with a lead-conjugated hapten, and the quality control line can be coated with a goat anti-chicken IgY antibody. In some embodiments, the detection line can be located on the side closer to the loading end, and the quality control line can be located on the side farther from the loading section. In some embodiments, the lead-conjugated hapten can be lead-conjugated bovine serum albumin, or lead-conjugated ovalbumin. In some embodiments, the concentration of the lead-conjugated hapten can be 0.5-5 ug/mL, and in some embodiments 1 ug/mL. The disclosed subject matter can have no special limitation on the source of the lead-conjugated hapten, and it may be a conventional commercially-available product, for example purchased from Beijing Deoping Biotechnology Co., Ltd. In some embodiments, the concentration of the goat anti-chicken IgY antibody can be 0.5-2 ug/mL, and in some embodiments 1.5 ug/mL. In some embodiments, by streaking the lead-conjugated hapten and the goat anti-chicken IgY antibody respectively at the position of the detection line and the position of the quality control line on the nitrocellulose membrane, after the membrane streaking is completed, drying can be achieved by baking at 45-65° C. for 2-6 h.

In some embodiments, the quality control can be a lead-containing buffer which can ensure the stability of lead nitrate and thus avoid precipitation, and the buffer can include the following components: a 0.5 mM nitric acid buffer, Tween 20 with a mass-to-volume ratio of 0.1%, bovine serum albumin with a percentage mass content of 0.5%, Proclin300 (used as a preservative) with a percentage mass content of 0.1%, and water as the solvent, with the pH value being 4.8-5.0. In some embodiments, the pH value can be selected to be capable of stabilizing the quality control, and suppressing hydrolysis of lead nitrate. In some embodiments, the quality control can be stored after lyophilization, and a lyophilization buffer for the lyophilization can use a nitrate buffer having a pH value of 4.5-4.8 as a basal buffer, and also can include 5-10 g/L of trehalose, 5-20 g/L of mannitol and Proclin300 with a percentage mass content of 0.1%. The lyophilization buffer disclosed herein can ensure the stability of the finished product after lyophilization. In some embodiments, the lyophilization can be vacuum lyophilization, and the time of the vacuum lyophilization can be 12-18 h. The disclosed subject matter can have no specific limitation on the pH adjustment method, and it can be adjusted by using a conventional pH adjuster of which the technical content is known in the art. In some embodiments, a detection card as prepared can be used to set values for quality controls, and after the values are assigned, the quality controls can be lyophilized separately to obtain quality controls of different concentrations, so as to facilitate the detection of subsequent samples. Particularly, in some embodiments, value setting of the quality controls can be conducted according to a calibration material which is used for source tracing and value assigning according to a national reference material, and different concentrations of the quality controls can be formulated into lyophilization buffers, lyophilized under vacuum for 12-18 hours to obtain the quality controls.

In some embodiments, the detection card can further include absorbent paper. The disclosed subject matter can have no specific limitation on the absorbent paper, and a conventional commercially-available absorbent paper for a detection card can be adopted.

In some embodiments, after the sample pad, the glass fiber membrane, the nitrocellulose membrane, and the absorbent paper are obtained, preparation of the detection card can be performed according to a conventional method. For example, the sample pad, the baked glass fiber membrane, the baked nitrocellulose membrane and the absorbent paper can be sequentially adhered to the bottom plate; then a bar cutting and casing process can be conducted, that is, a large reagent plate can be cut and then loaded into a reagent card, added with a desiccant and sealed with an aluminum foil bag, to obtain the detection card.

In some embodiments, the detection card can further include a card housing which can further include a back card and an upper cover. The back card can be provided with a detection-card slot in which the detection card is embedded. The upper cover can be provided with a test window and a sample loading well, where the position of the test window can be matched with those of the detection line and the quality control line, and the position of the sample loading well can be matched with that of the sample pad. In some embodiments, the card housing is preferably a plastic card housing.

In some embodiments, the sample that can be detected by the kit can include a blood sample and a urine sample. The urine sample can be treated by adding with a diluent and allowing to stand at room temperature for 5 minutes, wherein the diluent can include 50-200 mmol of the glycine buffer, 0.9% sodium chloride, 0.1% of S13, and 0.05% of the preservative Proclin300. Because different types of samples exist in different detection environments during detection, and complicated protein components in the samples bind with antibodies and fluorescent markers coated on the test paper card to different degrees, the detection result can be interfered, and thus non-specific and false signals, namely false positives, can appear in the detection line. To overcome such problem, a preprocessing operation on the samples can be carried out. When the sample is blood, the kit can further include a blood filter membrane. The blood sample disclosed herein can include whole blood, serum, plasma, and the function of addition of the blood filter membrane can be filtering blood cells from the whole blood. The disclosed subject matter can have no specific limitation on the source of the blood filter membrane, and a conventional commercially-available product of blood filter membrane that is known to those skilled in the art can be adopted. In some embodiments, the detection method with the kit disclosed herein can include the following steps: sampling: 20 ul of a serum sample can be taken by a pipette, added into a buffer, mixed well and allowed to stand at room temperature for 5 min, and the supernatant can be taken. Loading: a test paper card can be removed from a packaging bag, and 80 µl of the dilution of the above sample can be taken by a pipette and added into the sample loading well of the test paper card. Testing: After sample loading, the test paper card can be allowed to standing for 15 min at room temperature, and then placed into a dry-type fluoroimmunoassay quantitative analyzer to read the data. The time can be strictly controlled within 15 min. The dry-type fluoroimmunoassay quantitative analyzer can conduct measuring and analyzing treatments on optical signals to quantify the concentration of the material to be tested.

The kit disclosed herein adopts the principle of competitive immunochromatographic detection, and can be used in coordination with the immunoassay quantitative analyzer. The lead in a specimen can bind with the conjugate of the lead-specific antibody and the fluorescent microsphere coated on the glass fiber, to form an immunological complex of "fluorescent particle-antibody-antigen", which can then be chromatographed along the nitrocellulose membrane into the detection zone (T) to bind with the pre-coated lead-conjugated hapten, with its fluorescence intensity being inversely proportional to the lead content in the sample. The conjugate of the chicken IgY antibody and the fluorescent microsphere can be chromatographed into the quality control zone (C) and bind with the pre-coated goat anti-chicken IgY antibody on the quality control line. Therefore, as the residual concentration of the heavy metal lead in the sample increases, the color development of the detection line can be gradually faded as being inhibited; and the goat anti-chicken IgY antibody can be recognized and bound since the quality control line contains the goat anti-chicken IgY antibody thereon, and thus a control line can be developed to show that the result of product detecting is valid, no matter whether the sample contains the heavy metal lead.

The detection kit for quickly detecting a lead content in a sample can be further described in detail below with reference to specific examples, and the technical solutions of the disclosed subject matter can include, but are not limited to, the following examples.

Example 1

Figure 1:
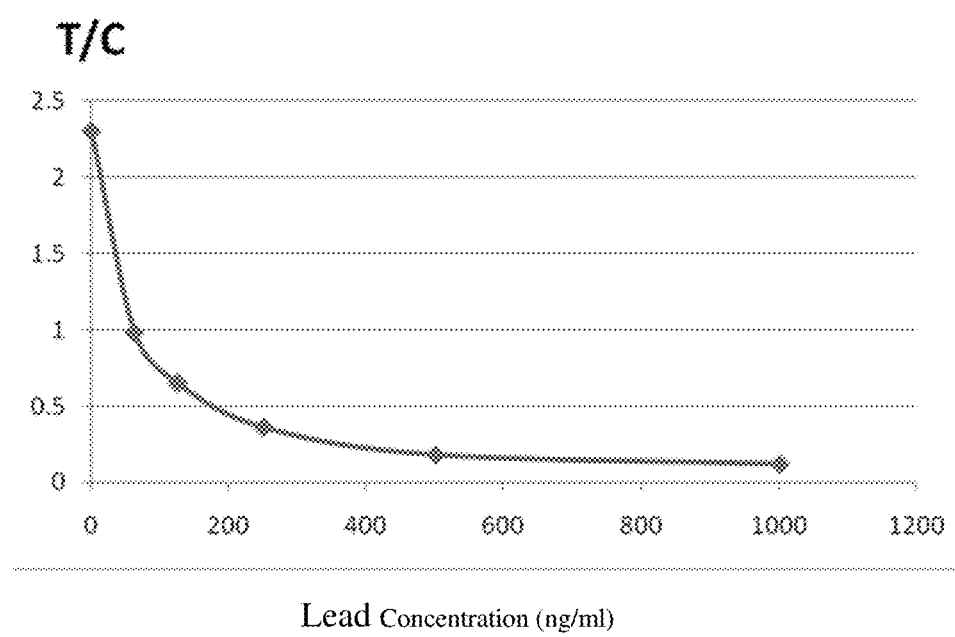
FIG. 1 is a calibration curve diagram as provided by Example 1 of the disclosed subject matter.
Figure 2:
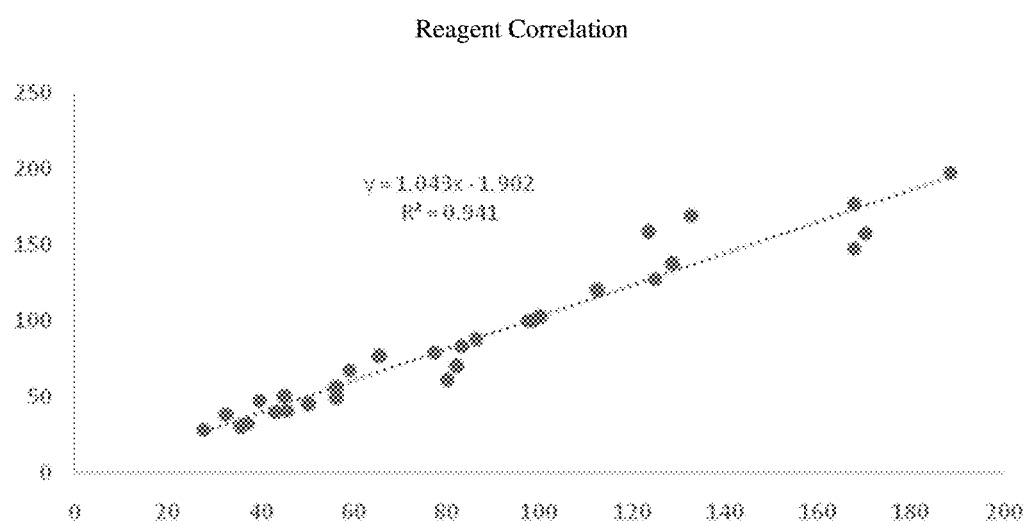
FIG. 2 is a diagram showing the correlation of reagents as provided in Comparative Example 1 of the disclosed subject matter.

Preparation of a Reagent Card:

Fluorescent microspheres with a particle size of 100 nm were used; two tubes were taken, the tube 1 was added with 1% of the fluorescent microspheres, 10 mg/ml of EDC, 3 ug/ml of the lead-specific antibody, mixed well for 2 h for conjugation, centrifuged at a speed of 8000-14000 r/min for 30 min, the supernatant was removed, the operations were repeated twice, and then 1% BSA 2.5 was added for blocking for 1 hour. The tube 2 was added with 1% of fluorescent microspheres, 10 mg/ml of EDC, and 50 ug of the chicken IgY antibody, mixed well for 2 h for conjugation, centrifuged at a speed of 8000-14000 r/min for 30 min, the supernatant was removed, the operations were repeated twice, and then 1% BSA was added for blocking for 1 hour; the prepared labeled conjugates were centrifuged, and re-suspended using 100 mmol of a resuspension buffer containing a boric acid buffer at a pH of 6.8, 2 g/L of sucrose, and 0.1% of Tween 20; after re-suspending, the re-suspensions were respectively mixed at 5:1 until the final mass/volume fraction was 0.2%, and the glass cellulose membrane was immersed in the resuspension buffer for 2 hours, and then baked for 1 hour; and by using a metal spraying membrane-streaking instrument, the label-containing conjugate re-suspension was sprayed onto the baked glass cellulose membrane, and then baked in an air dry oven at 65° C. for 2 hours after the metal spraying was completed;

loaded into a reagent card, added with a desiccant and sealed with an aluminum foil bag, to obtain the test paper card for detection;

Preparation of a Calibration Curve:

Quality controls of concentrations of 0, 62.5, 125, 250, 500 and 1000 ng/ml were respectively added dropwise onto the detection card with 3 replicate cards being set for each concentration, mixed well, and allowed to standing and chromatographed for 15 min, and then an immunofluorescence analyzer is used to read fluorescence signal values, so as to calculate the T/C value and thus establish a calibration curve (FIG. 1), where the X axis is the concentration of the quality control and the Y axis is the T/C value.

Detection of Sample Reproducibility:

The detection samples were added dropwise into sample loading wells with 10 replicates were set for each sample. The detection sample was a serum sample. Since a natural high-value sample could not be obtained due to the metabolic process of the heavy metal lead, the high-value sample was obtained by adding pure lead into a clinical serum sample (which explained the source of the high-value sample in the data). Reproducibility data of different levels of samples within a specific linear range was as shown in Table 1:

TABLE 1

Reproducibility of different samples

| Sample No. | Sample Concentration (ug/ml) Determination | | | | | | | | | | Average value | Standard Deviation | CV |
|---|---|---|---|---|---|---|---|---|---|---|---|---|---|
| | 1 | 2 | 3 | 4 | 5 | 6 | 7 | 8 | 9 | 10 | | | |
| 1 | 20.1 | 21.2 | 22.3 | 19.8 | 18.9 | 20.6 | 21.1 | 19.7 | 21.3 | 17.9 | 20.29 | 1.287072 | 6.34% |
| 2 | 50.6 | 51.8 | 49.8 | 52.3 | 52.9 | 48.9 | 49.1 | 55.7 | 52.6 | 56.8 | 52.05 | 2.642074 | 5.08% |
| 3 | 100.2 | 108.4 | 110.2 | 99.8 | 98.9 | 100.5 | 107.8 | 109.2 | 97.3 | 95.8 | 102.81 | 5.452716 | 5.30% |
| 4 | 201.9 | 210.2 | 219.3 | 198.3 | 197.3 | 201.4 | 205 | 210.3 | 197.9 | 197.9 | 203.95 | 7.273735 | 3.57% |
| 5 | 280 | 289.2 | 298.1 | 288.9 | 300.1 | 279.8 | 289.1 | 301.2 | 305 | 310.3 | 294.17 | 10.34387 | 3.52% |
| 6 | 310 | 319.3 | 320.9 | 324.4 | 350.1 | 300.5 | 304.2 | 321.3 | 325.1 | 329 | 320.48 | 13.99586 | 4.37% |
| 7 | 450 | 451.1 | 465 | 472.1 | 473.6 | 460.2 | 451.9 | 461.8 | 423.5 | 435.1 | 454.43 | 15.79902 | 3.48% |
| 8 | 600 | 599.8 | 567.9 | 583.7 | 610.2 | 600.8 | 610.3 | 620 | 612.9 | 604.7 | 601.03 | 15.21987 | 2.53% |
| 9 | 800 | 789.1 | 821.9 | 830.1 | 786.3 | 790.3 | 810.2 | 839.2 | 798.5 | 825.1 | 808.94444 | 20.10933 | 2.49% |
| 10 | 980 | 923.4 | 934.4 | 935.7 | 1000.1 | 932 | 945.3 | 956.2 | 998.2 | 980.3 | 961.1 | 29.32128 | 3.05% |

The nitrocellulose membrane (NC membrane) was cut into 30-31 cm/piece. 2 centrifuge tubes were taken and labeled as C and T, with C being used for the formulation of a coating solution for the goat anti-chicken IgY antibody, and T being used for the formulation of a coating solution for the lead-coupled hapten; the centrifuge tube T was added with 0.5 mg/L of the lead-coupled hapten (lead-BSA coated antigen), diluted by mixing well with a coating buffer (50 mmol of a boric acid buffer with the pH of 7.0 plus 0.1% of a Proclin300 preservative) until the concentration of the lead-coupled BSA (purchased from Beijing Deoping Biotechnology Co., Ltd.) was 1 mg/ml; the centrifuge tube C was added with 0.5 mg/L of the goat anti-chicken IgY antibody, then diluted by mixing well with the addition of the coating solution until the concentration of the goat anti-chicken IgY antibody was 1 mg/ml; and the membrane conjugate and the quality control line were streaked on the nitrocellulose membrane respectively at the positions of the T line and the C line, and then baked in an air dry oven at 65° C. for 2 hours after the membrane streaking was completed;

the sample pad, the blood filter membrane, the baked glass cellulose membrane, the baked nitrocellulose membrane, and the absorbent paper were sequentially adhered to the bottom plate; and a large reagent plate was cut and then It can be seen from Table 1 that, during the testing of the different concentrations of samples within the whole linear range, the CV of each detection result is less than 10%, indicating a good reproducibility and meeting the testing requirements.

Different concentrations of samples were detected within [10, 1,000] ng/mL, and the example results were as follows:

A sample having a high concentration close to the upper limit of the linear interval and a dilution of the sample were mixed into at least 5 dilution concentrations according to certain ratios with each dilution being tested for 3 times, and an average value of detection results for each dilution was determined separately. The correlation coefficient (r) of linear regression was calculated

TABLE 2

Detection of different gradients within the linear interval

| Linear Scale | 10 | 50 | 100 | 500 | 1000 |
|---|---|---|---|---|---|
| Measured value 1 | 12.3 | 64.3 | 120.3 | 531.3 | 968.9 |
| Measured value 2 | 9.8 | 55.9 | 120.3 | 520.3 | 978.3 |
| Measured value 3 | 10.5 | 58.3 | 113.2 | 510.2 | 978.2 |

TABLE 2-continued

Detection of different gradients within the linear interval

| Linear Scale | 10 | 50 | 100 | 500 | 1000 |
|---|---|---|---|---|---|
| Average value | 10.9 | 59.5 | 117.9 | 520.6 | 975.1 |
| Theoretical Value | 23.98 | 62.84 | 111.42 | 500.02 | 985.78 |
| Relative Deviation | −54.68% | −5.32% | 5.85% | 4.12% | −1.08% |
| Absolute Deviation | 13.11 | 3.34 | 6.52 | 20.58 | 10.64 |
| Correlation Coefficient r | 0.99943 | | | | |

It can be seen from Table 2 that, the correlation coefficient was greater than 0.99, which met requirements.

A normal sample ($C_0$) was added with a standard solution formulated from pure cadmium nitrate with a concentration close to a linear high value (200 μg/mL, with the relative deviation being within ±10%). The volume ratio of the added sample $C_S$ to the clinical sample $C_0$ is 1:19, and a sample C was formulated. The samples $C_0$ and C were measured respectively with 3 times of measurement for each, and then average values were calculated, and the recovery rates were calculated according to equation (1).

$$R = \frac{C \times (V_0 + V) - C_0 \times V_0}{V \times C_S} \times 100\% \quad (1)$$

wherein, R—a recovery rate
V—the volume of the added sample
$V_0$—the volume of the normal sample
C—the concentration determined after mixing
$C_0$—the concentration determined for the normal sample
$C_S$—concentration of the added sample

TABLE 3

Table of data for a recovery test

| | Blood | Mixed | High |
|---|---|---|---|
| 1 | 57.8 | 100.2 | 998.2 |
| 2 | 60.3 | 102.4 | 989.2 |
| 3 | 61.2 | 103.5 | 997.5 |
| Average value | 59.8 | 102.0 | 995.0 |
| Dilution ratio | 19 | 20 | 1 |
| Recovery rate | 91% | | |

As can be seen from Table 3, the recovery rate was between 85-115%, which met the requirements. The reagent accuracy was qualified and was not affected by the sample matrix.

Example 2

Preparation of a Reagent Card:

Fluorescent microspheres with a particle size of 120 nm were used, a tube 1 was added with 1% of the fluorescent microspheres, 10 mg/ml of EDC, and 1.5 ug/ml of the lead-specific antibody, mixed well for 2 h for conjugation, and centrifuged at a speed of 8000-14000 r/min for 30 min, the supernatant was removed, the operations were repeated twice, and then 1% BSA 2.5 was added for blocking for 1 hour. A tube 2 was added with 1% of the fluorescent microspheres, 10 mg/ml of EDC, and 50 ug of the chicken IgY antibody, mixed well for 2 h for conjugation, centrifuged at a speed of 8000-14000 r/min for 30 min, the supernatant was removed, the operations were repeated twice, and then 1% BSA was added for blocking for 1 hour; the prepared labeled conjugates were centrifuged, and re-suspended using 80 mmol of a resuspension buffer containing a glycine buffer at a pH of 6.0, 0.5-3.0 g/L of sucrose, and 0.1% of Tween 20; after re-suspending, the re-suspensions were mixed at 5:1, and the glass cellulose membrane was immersed in the resuspension buffer for 2 hours, and then baked for 1 hour; and by using a metal spraying membrane-streaking instrument, the label-containing conjugate re-suspension was sprayed onto the baked glass cellulose membrane, and then baked in an air dry oven at 65° C. for 2 hours after the metal spraying was completed;

the T line was the lead-coupled horse serum albumin at the concentration of 1 mg/ml; the C line was the goat anti-chicken IgY antibody at the concentration of 1 mg/ml; and the membrane conjugate and the quality control line were streaked on the nitrocellulose membrane respectively at the positions of the T line and the C line, and then baked in an air dry oven at 65° C. for 2 hours after the membrane streaking was completed;

the sample pad, the blood filter membrane, the baked gold standard pad, the baked nitrocellulose membrane, and the absorbent paper were sequentially adhered to the bottom plate; and a large reagent plate was cut and then loaded into a reagent card, added with a desiccant and sealed with an aluminum foil bag, to obtain the test paper card for detection;

Preparation of a Calibration Curve:

quality controls of concentrations of 0, 62.5, 125, 250, 500 and 1000 ng/ml were respectively added dropwise onto the detection card with 3 replicate cards being set for each concentration, mixed well, and allowed to standing and chromatographed for 15 min, and then an immunofluorescence analyzer is used to read fluorescence signal values, so as to calculate the T/C value and thus establish a calibration curve), where the X axis is the concentration of the quality control and the Y axis is the T/C value.

The calibration curve was prepared as in Example 1.

TABLE 4

Table of reproducibility data for two levels

| Quality Control | Sample Concentration (ng/ml) | | | | | | | | | | Average value | Standard Deviation | CV |
|---|---|---|---|---|---|---|---|---|---|---|---|---|---|
| | 1 | 2 | 3 | 4 | 5 | 6 | 7 | 8 | 9 | 10 | | | |
| 1 | 109 | 110 | 112 | 123 | 113 | 108 | 109 | 118 | 119 | 98 | 112 | 7.028 | 6.3% |
| 2 | 402 | 413 | 378 | 424 | 432 | 420 | 417 | 389 | 416 | 445 | 413.7 | 19.63 | 4.7% |

It can be seen from Table 4 that, CV (the correlation coefficient), of the two levels was not greater than 15%, which met the requirements.

TABLE 5

Table of detection data for different gradients within a linear interval

| Linear Scale | 10 | 50 | 100 | 500 | 1000 |
|---|---|---|---|---|---|
| Measured value 1 | 9.9 | 48.9 | 120.3 | 490.9 | 1000.3 |
| Measured value 2 | 9.8 | 55.9 | 109.3 | 519.2 | 978.3 |
| Measured value 3 | 10.5 | 46.8 | 130.2 | 487.3 | 978.2 |
| Average value | 10.1 | 50.5 | 119.9 | 499.1 | 985.6 |
| Theoretical Value | 17.64 | 56.82 | 105.80 | 497.62 | 987.38 |
| Relative Deviation | −42.94% | −11.07% | 13.36% | 0.31% | −0.18% |
| Absolute Deviation | 7.58 | 6.29 | 14.13 | 1.52 | 1.78 |
| Correlation Coefficient r | 0.99978 | | | | |

The correlation coefficient was greater than 0.99, which met requirements.

Comparative Example 1

Currently, in 30 provincial and municipal medical institutions in China, clinical examination a tungsten boat elemental analyzer for lead is widely used for measuring blood lead. This instrument is an atomic absorption spectrometer specialized for detecting blood lead by using the tungsten boat as an atomizer (Beijing Bohui Innovation Biotechnology Co., Ltd.). The measured sample is atomized in the tungsten boat by electric heating, so as to generate a large number of ground-state free atoms, thereby absorbing the characteristic spectral line of a measured element emitted by a hollow cathode lamp, and completing the measurement process. The use time of the tungsten boat should not be too long. Generally, a carbon deposition phenomenon would occur within about 200 times of use, affecting the accuracy of the sample loading. It is not appropriate to use the element lamp continuously for too many times after completion of the standard curve, and added national reference material should be added every 10 uses to monitor the sensitivity of the element lamp; and the experimental method of the disclosed subject matter could realize a rapid speed, a high throughput, a single-person packaging, good stability of the reagent when stored at room temperature, and high reproducibility.

Correlation of sample results: 76 aliquots of actual human blood samples were determined for blood lead by using the tungsten-boat lead element analyzer and the method of the disclosed subject matter, respectively, and meanwhile a standard material with a concentration value similar to that of the sample to be tested was used as a quality control. The value determined by the experimental method of the disclosed subject matter had a range of 27.9-470 µg/L.

TABLE 6

Comparison with lead data determined by the tungsten-boat lead element analyzer

| Sample Number | Test Reagent | Control Reagent |
|---|---|---|
| 1 | 27.9 | 29.3 |
| 2 | 35.7 | 30.1 |
| 3 | 37.3 | 33.3 |
| 4 | 45.3 | 39.9 |
| 5 | 66.8 | 59.5 |
| 6 | 59.9 | 58.3 |
| 7 | 75.3 | 65.2 |
| 8 | 70.3 | 61.2 |
| 9 | 87.6 | 79.8 |
| 10 | 73.2 | 85.9 |
| 11 | 86.5 | 89.6 |
| 12 | 97.7 | 100.9 |
| 13 | 113.2 | 109.7 |
| 14 | 128.7 | 137.8 |
| 15 | 180.3 | 150.3 |
| 16 | 187.9 | 176.9 |
| 17 | 200.3 | 203.5 |
| 18 | 210.3 | 206.2 |
| 19 | 250.3 | 256.3 |
| 20 | 263.1 | 269.2 |
| 21 | 276.2 | 286.2 |
| 22 | 290.3 | 295.3 |
| 23 | 320.3 | 312.1 |
| 24 | 335.4 | 42.1 |
| 25 | 365 | 372.5 |
| 26 | 395.2 | 401.2 |
| 27 | 420.2 | 430.2 |
| 28 | 421.3 | 432.1 |
| 29 | 435.6 | 445.2 |
| 30 | 455.6 | 460.2 |

The linear correlation was greater than 0.9, which met clinical requirements. It was as shown in Table 6. The correlation coefficient of lead data determined by the experimental method of the disclosed subject matter and the tungsten-boat lead element analyzer was greater than 0.9, the results were credible, and a rapid speed, a high throughput, a single-person packaging, good stability of the reagent when stored at room temperature, and high reproducibility could be realized.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A kit for rapidly detecting a lead content in a sample, the kit comprising a detection card and a quality control; wherein the detection card comprises a bottom plate, and a sample pad, a glass cellulose membrane, a nitrocellulose membrane and an absorbent paper which are arranged on the surface of the bottom plate sequentially from a loading end;
   wherein the sample pad is treated by soaking in a sample pad treatment buffer, and the sample pad treatment buffer includes an active protein and a surfactant;
   wherein the glass cellulose membrane is coated with: a conjugate of a lead specific antibody and a fluorescent microsphere, and a conjugate of a chicken IgY antibody and a fluorescent microsphere;
   wherein the nitrocellulose membrane is marked with a detection line and a quality control line, the detection line is coated with a lead-conjugated hapten, and the quality control line is coated with a goat anti-chicken IgY antibody; and wherein the lead-specific antibody in the conjugate of the lead-specific antibody and the fluorescent microsphere is a lead-specific murine monoclonal antibody.

2. The kit according to claim 1, wherein the sample pad treatment buffer uses one or more of a triethanolamine buffer, a boric acid-borate buffer, and a glycine buffer as a basal buffer.

3. The kit according to claim 1, wherein the active protein comprises one or more of fetal bovine serum, horse serum albumin and bovine serum albumin.

4. The kit according to claim 1, wherein the surfactant comprises one or more of S9, S13, and Tween80.

5. The kit according to claim 1, wherein the ratio of the conjugate of the lead-specific antibody and the fluorescent microsphere to the conjugate of the chicken IgY antibody and the fluorescent microsphere is 4:1 to 7:1.

6. The kit according to claim 1, wherein the fluorescent microsphere has a particle size of 80-220 nm.

7. The kit according to claim 5, wherein the fluorescent microsphere has a particle size of 80-220 nm.

8. A method for preparing the glass cellulose membrane of the kit according to claim 1 comprising:

soaking the glass cellulose membrane in a resuspension buffer for 1-2 h, and baking it for 1-2 h to obtain a preprocessed glass cellulose membrane;

respectively dissolving the conjugate of the lead specific antibody and the fluorescent microsphere and the conjugate of the chicken IgY antibody and the fluorescent microsphere in the resuspension buffer;

spraying the solution onto the preprocessed glass cellulose membrane, and baking;

wherein the resuspension buffer uses one or more of a phosphate buffer, a boric acid buffer, and a glycine buffer as a basal buffer of 50-200 mM having a pH value of 5.5-6.8, and further comprises 0.5-3 g/L of sucrose and a S9 with a percentage mass content of 0.1%.

9. The kit according to claim 1, wherein the quality control is a lead-containing buffer, and the buffer comprises the following components: a 0.5 mM nitric acid buffer, Tween 20 with a mass-to-volume ratio of 0.1%, bovine serum albumin with a percentage mass content of 0.5%, Proclin300 with a percentage mass content of 0.1%, and water as the solvent, with the pH value being 4.8-5.0.

10. The kit according to claim 1, wherein the quality control is stored after lyophilization, and a lyophilization buffer for the lyophilization uses a 0.5 mM nitric acid buffer having a pH value of 4.5-4.8 as a basal buffer, and also comprises 5-10 g/L of trehalose, 5-20 g/L of mannitol and Proclin300 with a percentage mass content of 0.1%.

11. The kit according to claim 9, wherein the quality control is stored after lyophilization, and a lyophilization buffer for the lyophilization uses a 0.5 mM nitric acid buffer having a pH value of 4.5-4.8 as a basal buffer, and also comprises 5-10 g/L of trehalose, 5-20 g/L of mannitol and Proclin300 with a percentage mass content of 0.1%.

* * * * *